United States Patent [19]
Matsuura et al.

[11] Patent Number: 5,634,791
[45] Date of Patent: Jun. 3, 1997

[54] MOUTH WASHER

[75] Inventors: Masahiro Matsuura; Yoji Kawamoto, both of Kadoma, Japan

[73] Assignee: Matsushita Electric Works, Ltd., Osaka, Japan

[21] Appl. No.: 490,148

[22] Filed: Jun. 14, 1995

[30] Foreign Application Priority Data

Jul. 26, 1994 [JP] Japan .................... 6-174103

[51] Int. Cl.$^6$ .................... A61C 17/00
[52] U.S. Cl. .................... 433/87; 433/88
[58] Field of Search .................... 601/162; 132/322; 433/87, 86, 85, 80, 141, 88

[56] References Cited

U.S. PATENT DOCUMENTS

| | | | |
|---|---|---|---|
| 1,398,527 | 11/1921 | Muspratt | 433/88 |
| 3,144,867 | 8/1964 | Trupp et al. | 601/162 |
| 3,654,502 | 4/1972 | Carmona et al. | 433/86 |
| 3,759,274 | 9/1973 | Warner | 132/322 |
| 3,902,510 | 9/1975 | Roth | 132/322 |
| 4,236,889 | 12/1980 | Wright | 433/88 |
| 4,326,549 | 4/1982 | Hinding | 132/322 |
| 4,979,503 | 12/1990 | Chernack | 433/88 |
| 5,069,233 | 12/1991 | Ritter | 432/322 |
| 5,183,035 | 2/1993 | Weir | 433/80 |
| 5,267,579 | 12/1993 | Bushberger | 132/322 |
| 5,279,314 | 1/1994 | Poulus et al. | 132/322 |

*Primary Examiner*—Paul J. Hirsch
*Attorney, Agent, or Firm*—Burns, Doane, Swecker & Mathis, L.L.P.

[57] ABSTRACT

A mouth washer has a nozzle substantially aligned with discharging direction of water pumpt, while a motor for driving the pump, a power source battery and a battery-charging secondary coil are disposed in series with the pumpt, and a water tank is provided along one side of such series disposition, whereby any hydraulic pressure loss upon jetting water out of the nozzle is reduced to realize a water jet under a sufficient hydraulic pressure, concurrently prolonging the life of the battery and maximizing the capacity of the water tank.

9 Claims, 7 Drawing Sheets

5,634,791

1

MOUTH WASHER

BACKGROUND OF THE INVENTION

This invention relates generally to a mouth washer and in particular to such mouth washer that which allows any hydraulic pressure loss upon jetting water out of a nozzle to be reduced for realizing the jetting under a sufficient hydraulic pressure, prolonging the life of power source battery, and maximizing the capacity of water tank.

Conventionally, the mouth washers which suck in water with a pump and jet the water out of the nozzle are arranged, as has been disclosed, for example, in Japanese Patent Laid-Open Publication No. 4-30642, to have the pump actuated by the power source battery of a storage battery type incorporated in the washer, so that water is sucked from the tank and jetted out of the nozzle. Further, the washer in this example is shown to be provided, underneath the water tank, with means for charging the power source battery. Similar type mouth washers have been disclosed in U.S. Pat. No. 4,108,167 and so on.

In the mouth washers of the kind referred to, on the other hand, the pump is so actuated, as driven by the power source battery, as to have water sucked from the water tank and jetted through a meandering path out of the nozzle, and there has been a problem that a hydraulic pressure loss is caused to occur when water is passed through the meandering path for being jetted so as to render a sufficient jetting pressure to be uneasy to attain and, consequently, the life of the power source battery is shortened. Further, as the battery charging means is disposed underneath the water tank, there arises another problem that the capacity of the water tank is restricted and can hardly be enlarged.

DESCRIPTION OF THE INVENTION

A primary object of the present invention is, therefore, to provide a mouth washer which is capable of realizing the water jet under a sufficient pressure with any hydraulic pressure loss reduced upon being jetted out of the nozzle, prolonging the life of the power source battery, and maximizing the capacity of the water tank.

According to the present invention, this object can be realized by a mouth washer comprising a pump for sucking water from a water tank, and a nozzle disposed to be substantially aligned with discharging direction of the pump, wherein the pump as well as a motor for driving the pump, a power source battery for actuating the motor, and a battery-charging secondary coil are disposed in series, and the water tank is provided along one side of the series disposition.

Accordingly in the present invention, the foregoing arrangement allows water sucked from the water tank to be jetted out of the nozzle substantially in the same direction as the discharging direction of the pump, without causing any hydraulic pressure loss. Further, any wasteful consumption of the power source battery is restrained while attaining a sufficient jetting pressure, eventually the life of the power source battery can be extended, the series disposition of the pump, the motor for driving the pump, the power source battery and the battery-charging secondary coil as well as the disposition of the water tank along one side of the said series disposition can be adopted, whereby it is made possible to provide the water tank of a height substantially equal to the whole height of the mouth washer on the one side, and the capacity of the water tank can be sufficiently enlarged.

Other objects and advantages of the present invention shall become clear as the description of the invention

2 advances in the followings as detailed with reference to preferred embodiments shown in accompanying drawings.

Figure 1:
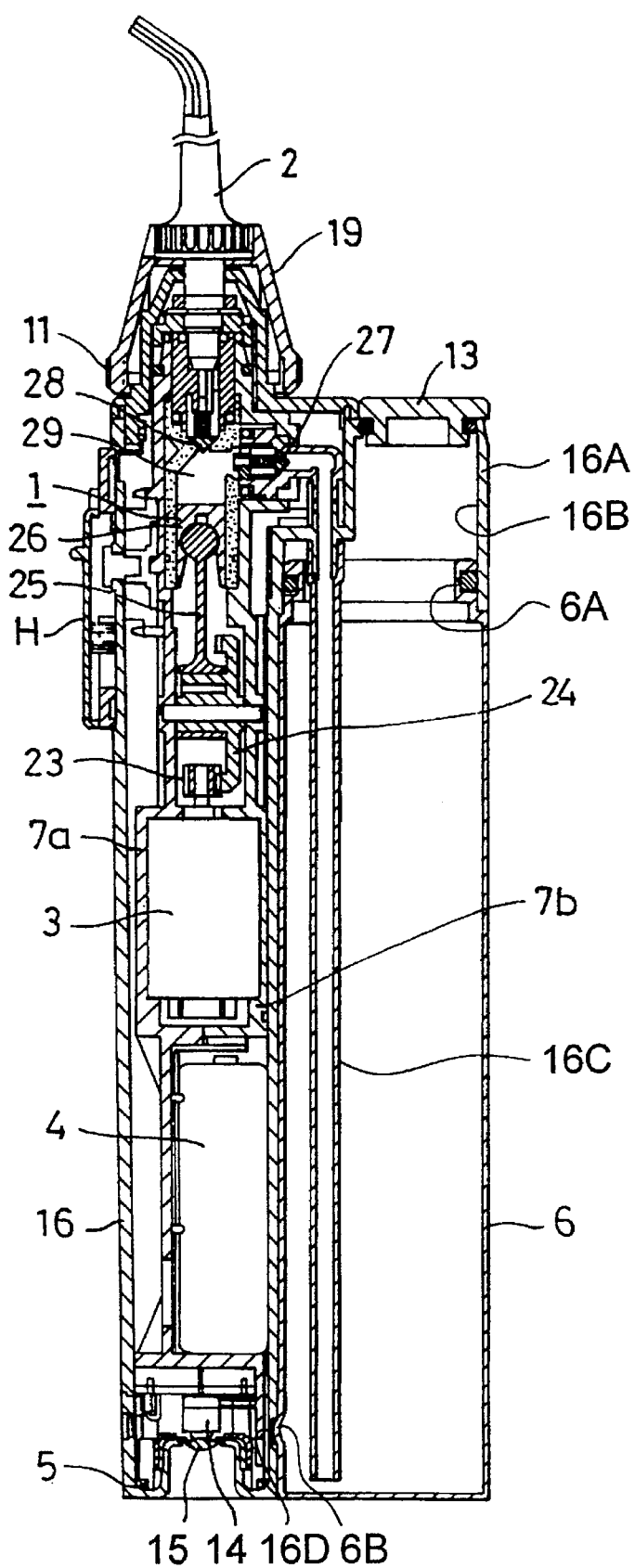
FIG. 1 shows in a vertically sectioned view the mouth washer in an embodiment according to the present invention.

While the present invention shall now be described with reference to the respective embodiments shown in the drawings, it should be appreciated that the intention is not to limit the invention only to the embodiments shown but rather to include all alterations, modifications and equivalent arrangements possible within the scope of appended claims.

DETAILED DESCRIPTION OF THE PREFERRED EMBODIMENTS

The mouth washer according to the present invention shall now be described with reference to the respective embodiments.

Figure 2:
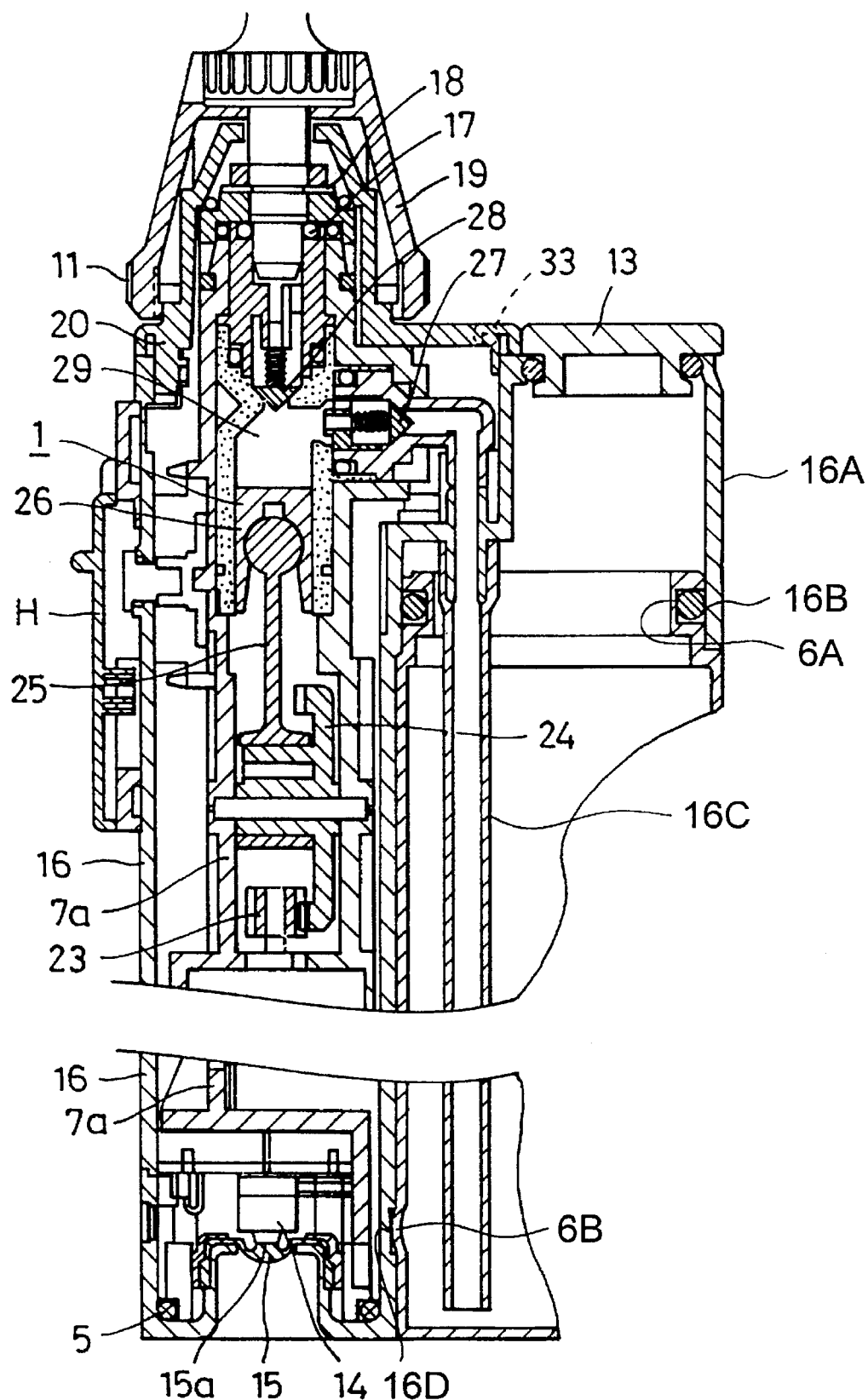
FIG. 2 is a fragmentary sectioned view as magnified of the washer in FIG. 1.
Figure 3A:
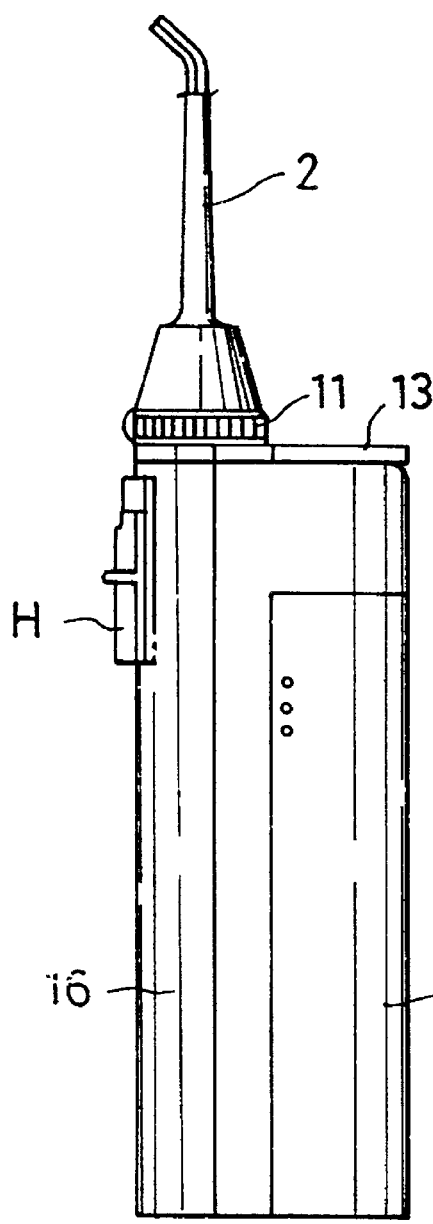
FIGS. 3A, 3B and 3C are a side elevation, a bottom plan and a front elevation respectively of the mouth washer shown in FIG. 1.
Figure 3C:
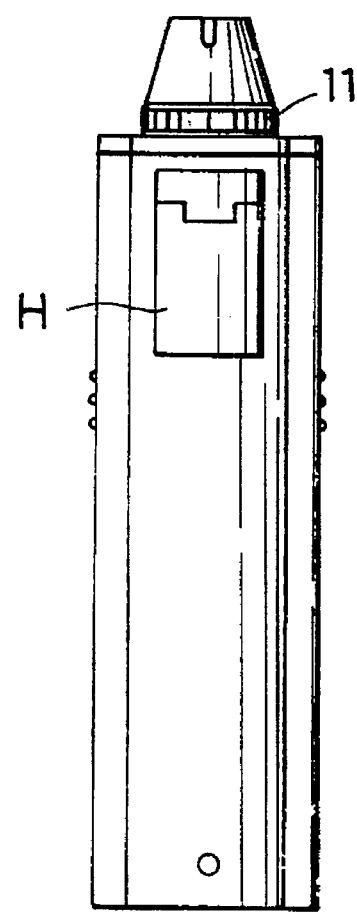
Figure 3B:
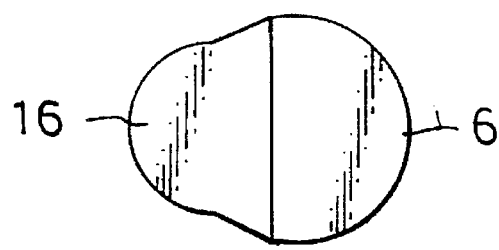

Referring here to FIGS. 1–3, there is shown an embodiment of the mouth washer in its entire section of FIG. 1, partial magnified section of FIG. 2, and outer appearance as viewed from different sides of FIGS. 3A–3C. In this mouth washer, a pump 1, a motor 3 for driving the pump and a power source battery 4 for the motor are fixedly held by two chassis halves 7a and 7b, and are housed in a device body 16. To a laterally projecting side part 16A of the body 16, a water tank 6 is detachably mounted. The side part 16A includes a downward facing opening 16B communicating by means of a tube 16C with a valve 27 (to be described later). The water tank 6 includes an upward facing opening 6A removably installed within the downward facing opening 16B. A projection 6B of the water tank 6 fits within a recess 16D of the device body to removably couple the water tank to the device body. Further, a nozzle 2 is detachably mounted to the top part of the body 16, to be positioned in alignment with discharging direction of the pump 1, and is held in position axially rotatably with a water-proof O-ring 17 and a wire spring 18 interposed. The nozzle 2 is engaged to a nozzle cover 19 to be integralized, while the nozzle cover 19 itself is rotatably screwed over a body cover 20. A rotation assisting means 11 comprising alternate grooves and strips is formed on the outer periphery at base end of the nozzle cover 19, for easy manual rotation of the nozzle 2. To the top of the water tank 6, a lid 13 is pivotably mounted through a hinge 33. In bottom part of the body 16, a micro-switch 14 is mounted, and a diaphragm 15 of an elastic material is internally fitted to an opening made in the bottom part to oppose an actuator of the micro-switch 14, so that an internal projection 15a of the diaphragm 15 is brought into engagement with the actuator of the micro-swich 14.

A pinion gear 23 mounted to an output shaft of the motor 3 is made in mesh with a face gear 24 rotatably supported on a shaft held across the two chassis halves 7a and 7b, a connecting rod 25 is coupled at an end slidably about an eccentric cam shaft of the face gear 24 and at the other rounded end to a piston 26, for advance and retreat motion, resulting in a reciprocating motion of the piston 26 in a cylindrical pressure chamber (pump chamber) 29 for a compression and depression in the chamber 29, as will be readily appreciated. The pressure chamber 29 is provided with a water suction valve 27 for communication with the interior of the water tank 6 and with a water discharge valve 28 for communication with the nozzle 2, so that the suction valve 27 is closed but the discharge valve 28 is opened by a raised pressure in the chamber 29 and a pressurized water can be jetted out of the nozzle 2.

Thus, the motor 3 rotated causes, through the pinion gear 23, face gear 24 and connecting rod 25, the piston 26 to be vertically driven for the reciprocating motion. With this reciprocating motion of the piston 26, the water suction and discharge valves 27 and 29 are alternately driven to be opened and closed by fluctuating pressure in the pressure chamber 29, and water is sucked from the water tank 6 into the chamber and discharged towards the nozzle 2 to be jetted thereout.

Since in this case the nozzle 2 is disposed in alignment with the discharge direction of the pump 1, water flow is smoothed, any pressure loss due to variation in flowing direction is eliminated, and water can be efficiently jetted out of the nozzle 4. That is, water can be jetted out of the nozzle 2 under a sufficient pressure, as a result of which a consumed power of the source battery 4 is reduced, to be contributive to a remarkable extension of battery life.

Since, in the foregoing arrangement, the pump 1, motor 3, battery 4 and secondary coil 5 are disposed in series relationship to one another and are integralized as held by the two chassis halves 7a and 7b, the assembling work is easy, and the mouth washer can be made easier in the handiness since the body 16 having a switch lever H is made thin.

On the other hand, the nozzle cover 19 is made thicker in its handling portion and is disposed closer to gripping part of the body 16, so that the nozzle cover 19 can be easily operated at the rotation assisting means 11 even with a hand which gripping the body 16, so that water jetting direction can be made variable during the use.

When water is to be supplied, the supply can be enabled only by rotating the lid 13 about the hinge 33 into open position, and the water tank 6 can be easily mounted and detached.

Figure 4:
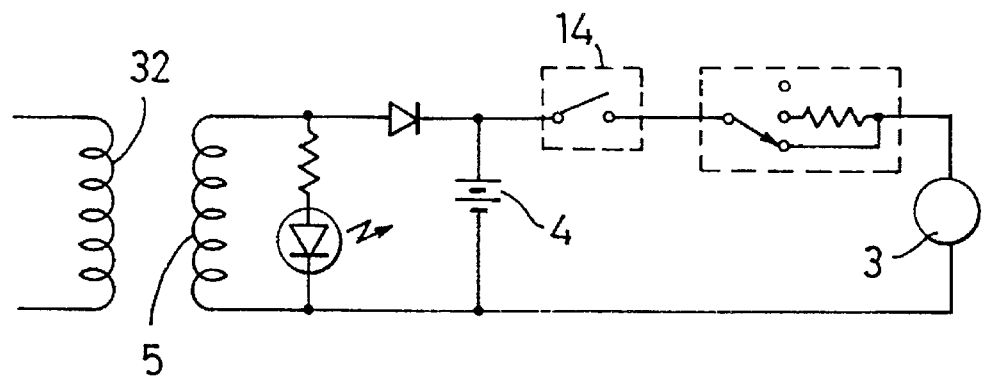
FIG. 4 shows schematically an electric circuit of the mouth washer, together with an associated primary coil of a battery charging means.
Figure 5:
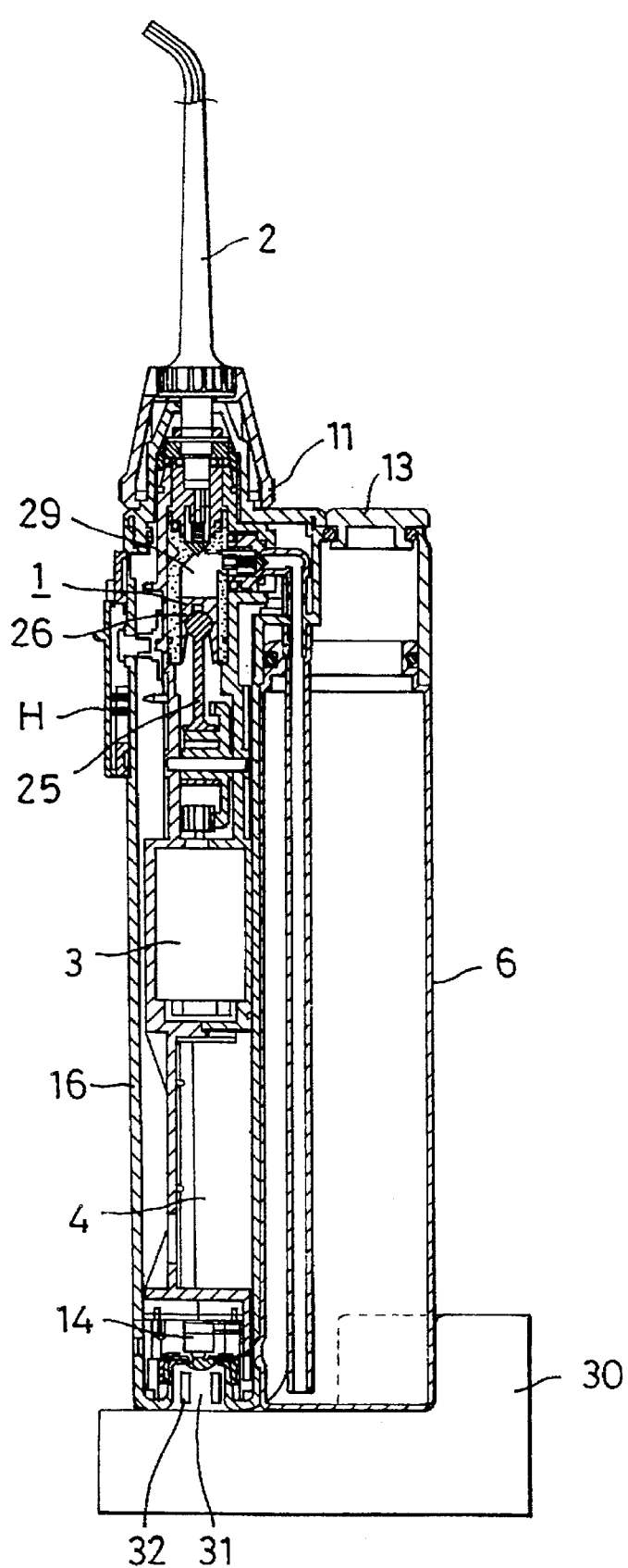
FIG. 5 schematically shows a state in which the mouth washer of FIG. 1 is mounted on a battery charger.

In FIG. 4, there is shown an electric circuit including the motor 3, battery 4, micro-switch 14 interposed between the motor and battery, and secondary coil 5 to which a primary coil 32 of a separate battery charger is shown as opposed. When, as shown in FIG. 5, the mouth washer is place on a battery charger stand 30, a projection 31 carrying the primary coil 32 of the stand 30 is fitted in the bottom opening of the body 16 to push up the diaphragm 15 with the own weight of the body 16 added, the micro-switch 14 can be thereby reliably turned off while assuring the waterproofness of the body 16 with the diaphragm 15, and the battery 4 can be reliably charged through the secondary coil 15 here opposed to the primary coil 32.

Figure 6A:
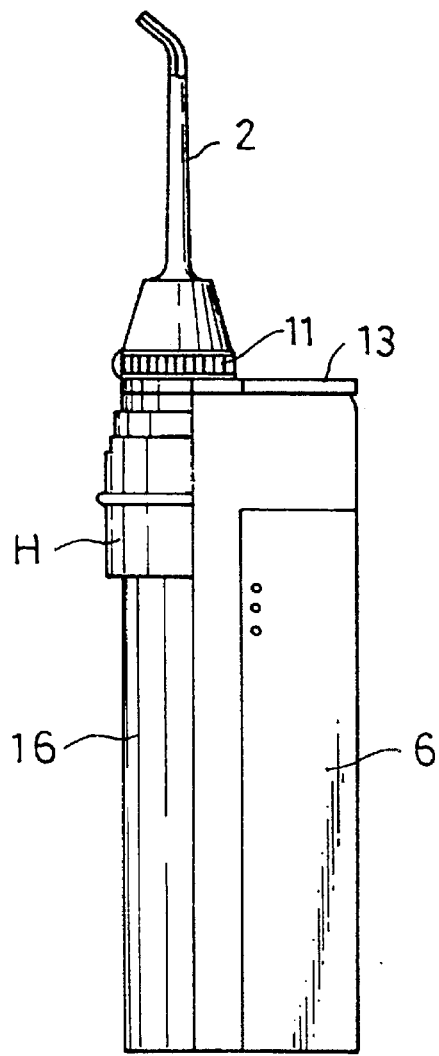
FIGS. 6A and 6B are a side elevation and a front elevation respectively of the mouth washer in another embodiment of the present invention.
Figure 6B:
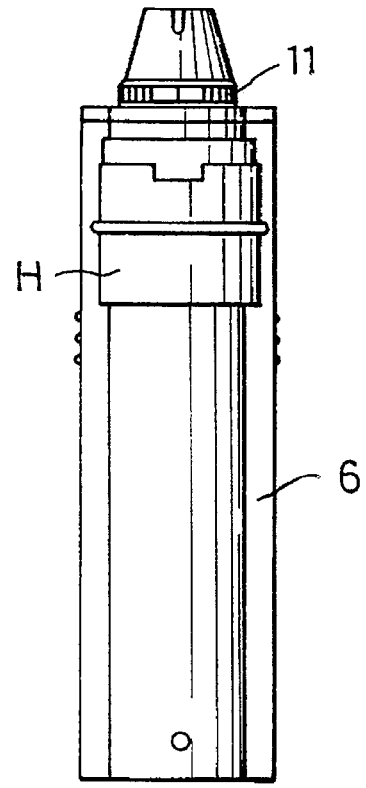

In FIGS. 6A and 6B, there is shown another embodiment in which the switch lever H is expanded to be 180 degrees wide on the front side of the body 16, and the body 16 including the water tank 6 is considerably enlarged. In this case, an ordinary arrangement of the mouth washer does not allow a finger of a hand which gripping the body 16 to reach the front side of the body 16 and the switch lever H cannot be operated with the single hand, but the present embodiment the constituent elements of which is arranged extremely compactly so that the operation of the switch lever H with the single gripping hand can be made easier.

Figure 7A:
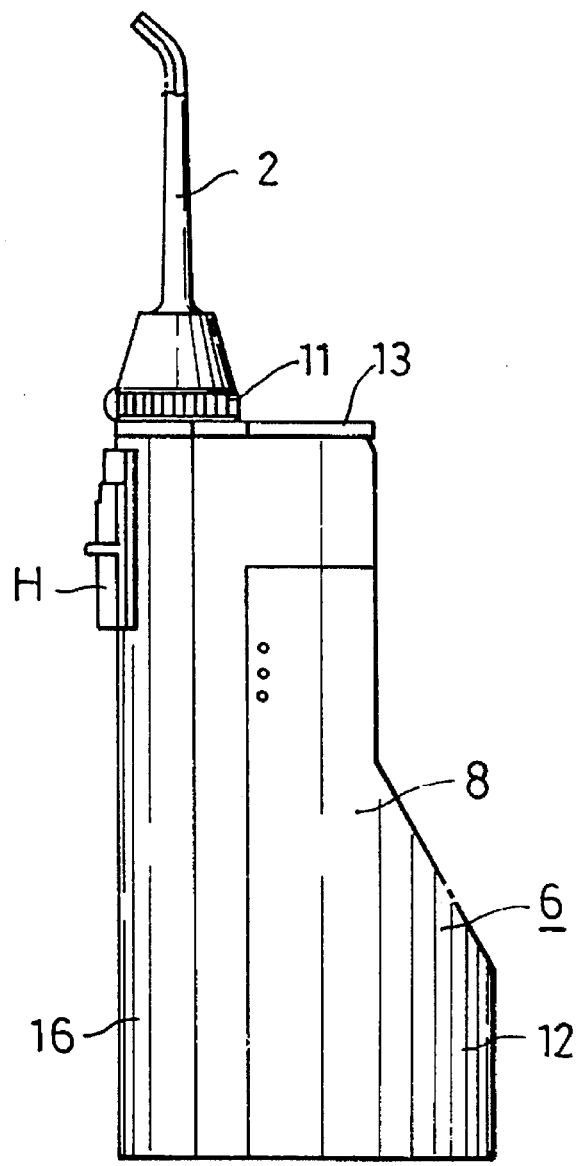
FIGS. 7A, 7B and 7C show in a side elevation, bottom plan and front elevation respectively another embodiment of the present invention.
Figure 7C:
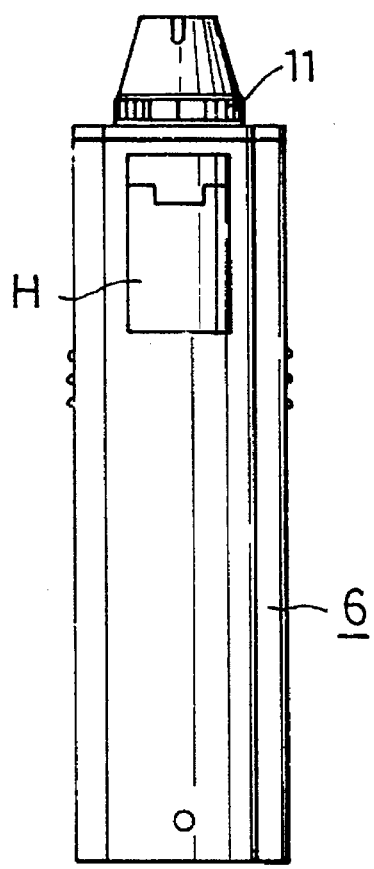
Figure 7B:
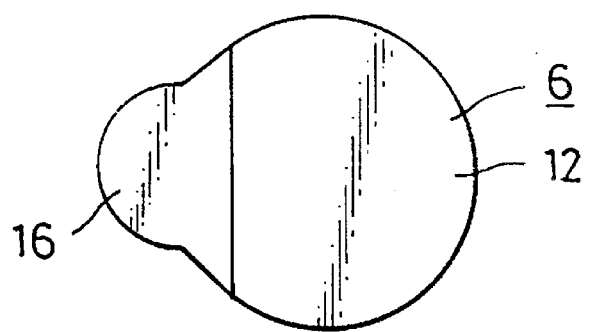
Figure 8A:
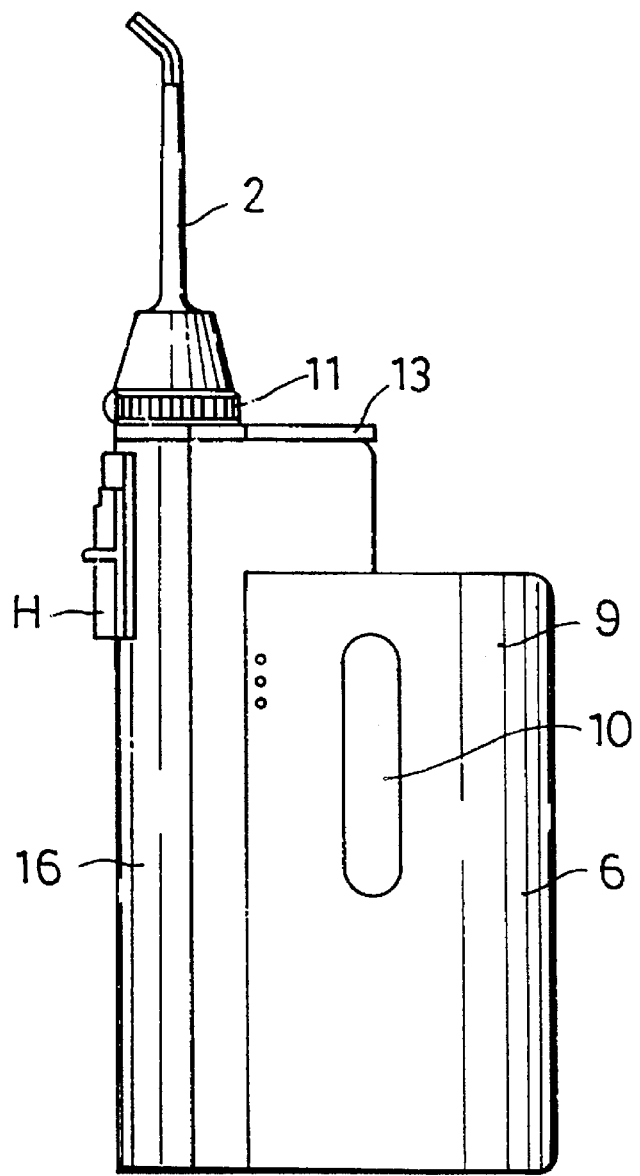
FIGS. 8A, 8B and 8C also show in a side elevation, bottom plan and front elevation respectively still another embodiment of the present invention.
Figure 8C:
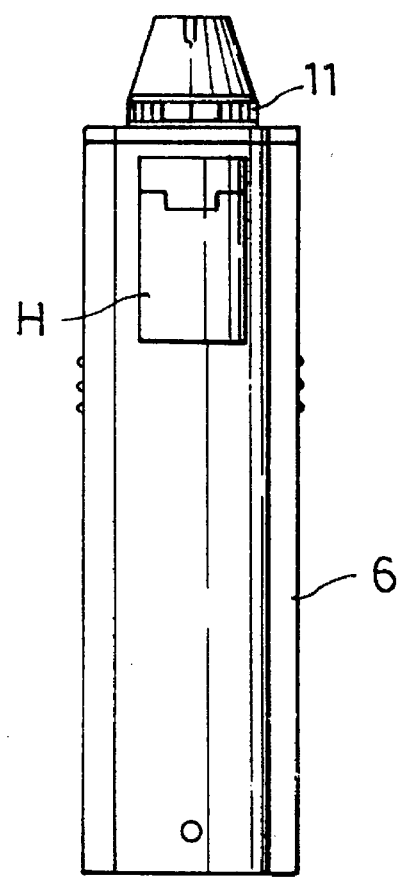
Figure 8B:
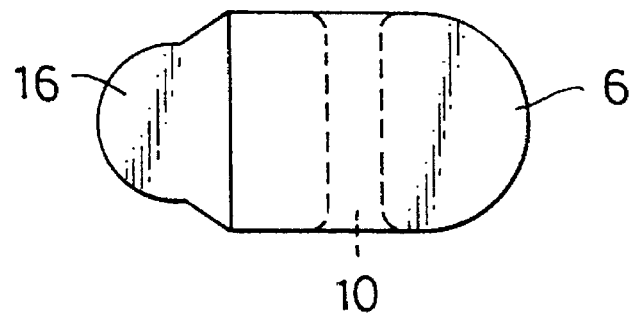

In FIGS. 7A–7C and FIGS. 8A–8C, further embodiments of the present invention in which the water tank 6 is modified are shown. Generally, the referenced type water tank 6 made larger for a longer term use with a single supply of water renders the mouth washer to be difficult to be operated with one hand. In the embodiment of FIGS. 7A–7C, therefore, the water tank 6 is enlarged at its lower part 12 but is constricted at intermediate part 8 so as to be kept thin at the upper part for use as the gripping part allowing the easy one-hand operation, while the capacity of water is increased for eventual extension of the term of use. In the embodiment of FIGS. 8A–8C, further, the water tank 6 is made entirely thicker with a rearward expanded part 9 but provided with an intermediate through hole 10 extending substantially along inherent rear side line of the body 16, for allowing the user's fingers inserted through the hole 10 for the easy gripping and one-hand operation, while increasing the capacity of water and extending the term of use.

Since in the present invention of the foregoing arrangement the water jetting nozzle is disposed to be substantially in alignment with the water discharging direction of the pump, in particular, it is enabled to jet the water sucked from the tank 6 and out of the nozzle substantially in the same direction as the discharging direction of the pump, to have the water jetting executed with the hydraulic pressure loss remarkably reduced, to obtain a sufficient jetting pressure while restraining any wasteful consumption of the battery power, and thus to realize the long term extension of the life of the power source battery. Further, since the pump, motor for driving the pump, power source battery, and battery charging secondary coil are disposed in series and the water tank is disposed along one side of such series disposition, there arises such advantage that the water tank can be provided to lie along the entire height of the side of the mouth washer, so that the water tank can be provided sufficiently large in the capacity.

What is claimed is:

1. A mouth washer comprising:
    a device body having longitudinally spaced top and bottom ends,
    a pump having a water discharge valve and a water suction valve and disposed inside an upper portion of the device body,
    a water jetting nozzle fitted to the top end of the device body to be in substantial longitudinal alignment with the discharge valve,
    a motor disposed in the device body for driving the pump,
    a power supply disposed inside a bottom portion of the device body for supplying electric power to the motor, the nozzle, pump, motor and power supply being disposed in substantial longitudinal alignment with each other and with the discharge valve, and
    a water tank disposed along one side of the device body and detachably coupled thereto.

2. The mouth washer according to claim 1 which further comprises a pair of chassis halves for fixedly holding said pump, motor and power source in said substantial longitudinal alignment, said chassis halves being housed in said device body.

3. The mouth washer according to claim 1 wherein said device body includes a switch lever mounted on a front side of the device body for actuation of said motor, the switch lever extending about 180 degrees around an outer periphery of the device body.

4. The mouth washer according to claim 1 wherein said water tank is formed to have a thinner top part acting as a gripping part of the washer and an expanded lower part continued through an intermediate constricted part to the thinner top part.

5. The mouth washer according to claim 1 wherein said water tank includes a through hole accommodating fingers of a user's hand for gripping the washer.

6. The mouth washer according to claim 1 wherein said device body is provided at a portion adjacent to said top end with a lid mounted pivotably to said portion, said water tank being coupled to said portion for being opened and closed by said lid.

7. The mouth washer according to claim 6, wherein the portion of the device body having the lid constitutes a lateral projection of the device body on the side thereof on which the water tank is coupled, the projection having a downward facing opening communicating with the water suction valve of the pump, and the water tank having an upward facing opening removably inserted in the downward facing opening of the projection.

8. The mouth washer according to claim 1 wherein a micro-switch capable of turning off an electric circuit from said power source battery to said motor and a diaphragm allowing said micro-switch to be operable from the exterior while keeping the micro-switch water-proof are provided on said washer.

9. The mouth washer according to claim 1, wherein the power supply comprises a rechargeable battery, a microswitch interposed between the motor and the battery, and a secondary coil disposed adjacent to the bottom end adapted to be accessible to a primary coil of a separate battery charger, the bottom end being provided with a flexible diaphragm allowing the micro-switch to be actuated in response to a mounting of the bottom end to a battery charger to disconnect the battery from the motor.

* * * * *